United States Patent
Graham

(10) Patent No.: US 9,423,336 B2
(45) Date of Patent: Aug. 23, 2016

(54) SYSTEMS AND METHODS FOR PARTICLE SENSING AND CHARACTERIZATION

(71) Applicant: Beckman Coulter, Inc., Brea, CA (US)

(72) Inventor: Marshall Donnie Graham, Nicholasville, KY (US)

(73) Assignee: Beckman Coulter, Inc., Brea, CA (US)

( * ) Notice: Subject to any disclaimer, the term of this patent is extended or adjusted under 35 U.S.C. 154(b) by 81 days.

(21) Appl. No.: 14/160,465

(22) Filed: Jan. 21, 2014

(65) Prior Publication Data

US 2014/0203825 A1 Jul. 24, 2014

Related U.S. Application Data

(60) Provisional application No. 61/756,096, filed on Jan. 24, 2013.

(51) Int. Cl.
*G01N 27/00* (2006.01)
*G01R 27/08* (2006.01)
*G01N 15/12* (2006.01)
*G01M 1/00* (2006.01)

(52) U.S. Cl.
CPC ............... *G01N 15/12* (2013.01); *G01M 1/00* (2013.01)

(58) Field of Classification Search
CPC ............................... G01N 15/12; G01N 1/00
USPC ............................... 324/71.4, 693, 71.1, 699
See application file for complete search history.

(56) References Cited

U.S. PATENT DOCUMENTS

| | | | |
|---|---|---|---|
| 2,656,508 A | 10/1953 | Coulter | |
| 3,628,140 A | 12/1971 | Hogg et al. | |
| 4,348,107 A | 9/1982 | Leif | |
| 4,515,274 A | 5/1985 | Hollinger et al. | |
| 4,760,328 A | 7/1988 | Groves | |
| 4,791,355 A | 12/1988 | Coulter et al. | |
| 5,125,737 A | 6/1992 | Rodriguez et al. | |
| 5,616,501 A | 4/1997 | Rodriguez et al. | |
| 6,111,398 A * | 8/2000 | Graham ............. | G01N 15/1218 324/71.4 |
| 6,175,227 B1 | 1/2001 | Graham et al. | |
| 6,259,242 B1 | 7/2001 | Graham et al. | |
| 8,189,187 B2 | 5/2012 | Graham et al. | |

* cited by examiner

*Primary Examiner* — Farhana Hoque
(74) *Attorney, Agent, or Firm* — Kilpatrick Townsend & Stockton LLP

(57) ABSTRACT

Systems and methods are provided for sensing and characterizing small particles, and in particular blood cells suspended in a liquid medium. Exemplary systems include a volumeter conduit having a central region of higher electrical resistivity disposed between a first and second distal region of lower electrical resistivity, and a current source and sensing circuit module in electrical connectivity with the first and second distal regions. The module provides an electrical excitation current to the first and second distal regions to establish a particle-sensitive zone within the conduit, and detects current changes occasioned by particles of the biological sample passing through the particle-sensitive zone.

20 Claims, 6 Drawing Sheets

SYSTEMS AND METHODS FOR PARTICLE SENSING AND CHARACTERIZATION

CROSS-REFERENCES TO RELATED APPLICATIONS

This application is a nonprovisional of, and claims the benefit of priority to, U.S. Provisional Patent Application No. 61/756,096 filed Jan. 24, 2013. This application is also related to U.S. Pat. Nos. 6,111,398, 6,175,227, and 6,259,242. The entire content of each of the above filings is incorporated herein by reference.

BACKGROUND OF THE INVENTION

Embodiments of the present invention relate in general to systems and methods for sensing and characterizing small particles, and in particular to techniques for detecting and evaluating blood cells suspended in a liquid medium having an electrical impedance per unit volume which differs from that of the cells.

A seminal method for sensing particles suspended in a liquid medium is described in U.S. Pat. No. 2,656,508 to Wallace H. Coulter. Over the past several decades, a broad variety of devices based on the Coulter principle described therein have been proposed, including highly automated hematology implementations.

Although such developments provide clinically useful devices for analyzing biological samples of an individual, still further improvements are desirable. For example, there is a continuing need for accurate and cost effective ways to analyze particles, and in particular blood cells of a biological sample obtained from a human individual. Embodiments of the present invention provide solutions for at least some of these outstanding needs.

BRIEF SUMMARY OF THE INVENTION

In accordance with embodiments of the present invention there is provided systems and methods for sensing and characterizing particles by the Coulter principle. Particle evaluation systems may be embodied in devices having a two-terminal configuration where both excitation and sensing functions are provided by or facilitated by conduit walls of an aperture. In some instances, the operation of devices may involve the use of low current densities which leads to little or no electrolysis (and corresponding gas bubble generation) which may otherwise interfere with detection and sizing of particles going through a composite conduit. For example, operation of the device may avoid or lessen the production of high field gradients near the join of an entry field amending unit and an insulative center of a field amending sandwich.

Exemplary particle evaluation systems include a volumeter assembly through which a liquid suspension of particles to be sensed and characterized can be made to pass, and a liquid containment system that holds a particle suspension which is passed through a conduit of the volumeter assembly. The volumeter assembly can be constructed such that the electrical resistivity of a wall defining the volumeter conduit varies in an axisymmetric manner along the conduit length (i.e., in a direction parallel to the flow of suspension through the conduit). In some instances, the conduit provides a central region of high electrical resistivity which is smoothly contiguous on its opposing boundaries to distal regions of substantially lesser electrical resistivity. Such distal regions can also be referred to as field amending units. The peripheral field amending units and intervening central substrate can provide a hydrodynamically smooth conduit containing wall.

The evaluation systems and methods disclosed herein are well suited for use in analyzing any of a variety of particles, including blood cells such as white blood cells, red blood cells, platelets, and other components of blood or biological samples. In some instances, particle evaluation systems can be implemented as or part of hematology systems for use in clinical, laboratory, or other biomedical settings. In some instances, particle evaluation systems can be implemented for industrial particle analysis applications.

Particle evaluation systems may also include electronic circuitry in operative association with the field amending units. Such circuitry can be configured to produce electrical excitation current through the volumeter conduit and also to monitor the amplitude of the electrical current through the volumeter conduit to sense the characteristics of particles passing through said conduit. In some instances, the central region of high electrical resistivity can be provided by a sapphire substrate, and the electronic circuitry associated with the distal regions can be formed by integrated-circuit techniques. In some cases, particle evaluation systems can be constructed without including certain features used in known systems, such as hydrodynamically focused flow and sweep flow. In many cases, particle evaluation systems as disclosed herein allow for reduced coincidence volumes.

Particle evaluation systems according to embodiments of the present invention can also provide simplified apparatus construction features and reduced building costs. Further, such systems can be provided in convenient forms for a broad range of particle sensing and characterizing applications. For example, minimal AC or DC versions packaged as remote transducers may be useful in many process applications, where they can be adapted to detect particles in the normal fluid flow. Further, DC versions may be adapted into instruments serving solute-analytic functions, thereby providing a particle detection, sizing, or characterization function as well. In some instances, a small hand-held, battery-powered version (e.g. a dipstick Coulter counter) may be useful in marine biology. A similar version may be useful in environmental studies at remote sites, and the like. In some instances, such an instrument may include a rubber bulb, a plastic bellows, or other fluid control means, to draw or express a set volume of sample suspension through the volumeter conduit of the particle evaluation system. In some instances, a micro-pipette having highly adjustable volume-aspiration mechanism can be used to draw or express a set volume of sample suspension through the volumeter conduit of the particle evaluation system.

In many embodiments, the particles to be characterized are suspended in a liquid medium having an electrical impedance per unit volume which differs from that of the particles. The particles pass substantially one at a time through an electrically excited field-amending volumeter conduit while changes in electrical current through the conduit are monitored using the field amending units.

All features of the described systems are applicable to the described methods mutatis mutandis, and vice versa.

In one aspect, embodiments of the present invention encompass systems and methods for evaluating particles of a biological sample obtained from an individual. Exemplary systems may include a volumeter assembly having a conduit adapted to receive a fluid suspension containing the particles therethrough. The conduit can define an axial conduit wall length having a central region of higher electrical resistivity disposed between a first distal or peripheral region of lower electrical resistivity and a second distal or peripheral region of lower electrical resistivity. The system may also include a first chamber in fluid communication with a first orifice of the volumeter assembly conduit, where the first chamber is adapted to contain at least a first portion of the fluid suspension, and a second chamber in fluid communication with a second orifice of the volumeter assembly conduit, where the second chamber is adapted to contain at least a second portion of the fluid suspension. Further, the system may include a current source and sensing circuit module in electrical connectivity with the first and second distal regions of the volumeter assembly. The current source and sensing circuit module can be configured to provide an electrical excitation current to the first and second distal regions to establish a particle-sensitive zone within the conduit, and to detect current changes occasioned by particles of the biological sample passing through the particle-sensitive zone. In some instances, the central region of the conduit wall length is provided by a layer of material having high electrical resistivity, and the first and second distal regions of the conduit wall length are provided by a first layer of material having a lower electrical resistivity and a second layer of material having a lower electrical resistivity, respectively. In some instances, the conduit wall length is provided by a semiconductor wafer which is doped with an electrically active impurity to provide the central region of higher electrical resistivity disposed between the first distal region of lower electrical resistivity and the second distal region of lower electrical resistivity. In some instances, the conduit wall length is provided by a unitary assembly having three complementary and contiguous ceramic elements, where a center ceramic element of the unitary assembly is substantially pure and two outer ceramic elements of the unitary assembly contain either a conductive ceramic or a ceramic infiltrated with a metallic material to enhance the conductivity thereof, and where the conduit is formed by through-holes respectively formed in the three ceramic elements. In some instances, the conduit wall length is provided by a unitary assembly having three complementary and contiguous elements, where a center element of the unitary assembly is made of a substantially pure ceramic and two outer elements of the unitary assembly are made of a metallic material, and where the conduit is formed by through-holes respectively formed in the three elements. In some instances, the central region of the axial conduit wall length is provided by a substrate of dialectic material, and the first distal region of lower electrical resistivity and the second distal region of lower electrical resistivity are provided by first and second conductive collars, respectively. In some instances, the volumeter assembly conduit has a circular cross-section. In some instances, the first and second distal regions of the axial conduit wall length are respectively provided by a material such as metals of the platinum group, gold, nickel, tungsten, titanium, alloys of the metals, silicon carbide, titanium carbide, or tungsten carbide. In some instances, the material providing the first distal region differs from the material providing the second distal region. In some instances, the central region of the axial conduit wall length is provided by a material such as sapphire, ruby, alumina, quartz, glass, beryllia, silicon carbide, titanium carbide, tungsten carbide, or a lossy dielectric.

In another aspect, embodiments of the present invention encompass methods of evaluating particles of a biological sample obtained from an individual. Exemplary methods may include transmitting a fluid suspension containing the particles through a volumeter assembly conduit, where the conduit defines an axial conduit wall length having a central region of higher electrical resistivity disposed between a first distal region of lower electrical resistivity and a second distal region of lower electrical resistivity. Methods may also include providing an electrical excitation current to the first and second distal regions with a current source and sensing circuit module in electrical connectivity with the first and second distal regions, so as to establish a particle-sensitive zone within the conduit, and detecting current changes occasioned by the particles of the biological sample passing through the particle-sensitive zone with the current source and sensing circuit module via the first and second distal regions.

In still another aspect, embodiments of the present invention encompass systems for evaluating particles of a biological sample obtained from an individual, where exemplary systems include a volumeter assembly, an electrical source, and a sensing circuit. In some embodiments, the volumeter assembly has a conduit adapted to receive a fluid suspension containing the particles therethrough, where the conduit defines an axial conduit wall length having a central region disposed between a first peripheral region and a second peripheral region, and where the central region has an electrical impedance greater than electrical impedances of the first and second peripheral regions. In some embodiments, the electrical source is in operative association with, and is configured to provide electrical excitation to, the first and second peripheral regions. In some embodiments, the sensing circuit is in operative association with the first and second peripheral regions, and is configured to detect impedance changes occasioned by particles of the biological sample passing through the first and second peripheral regions.

The above described and many other features and attendant advantages of embodiments of the present invention will become apparent and further understood by reference to the following detailed description when considered in conjunction with the accompanying drawings.

DETAILED DESCRIPTION OF THE INVENTION

Embodiments of the present invention encompass systems and methods for sensing and characterizing particles. In some instances, particle evaluation systems can be provided as handheld devices which operate upon the Coulter principle.

Figure 1:
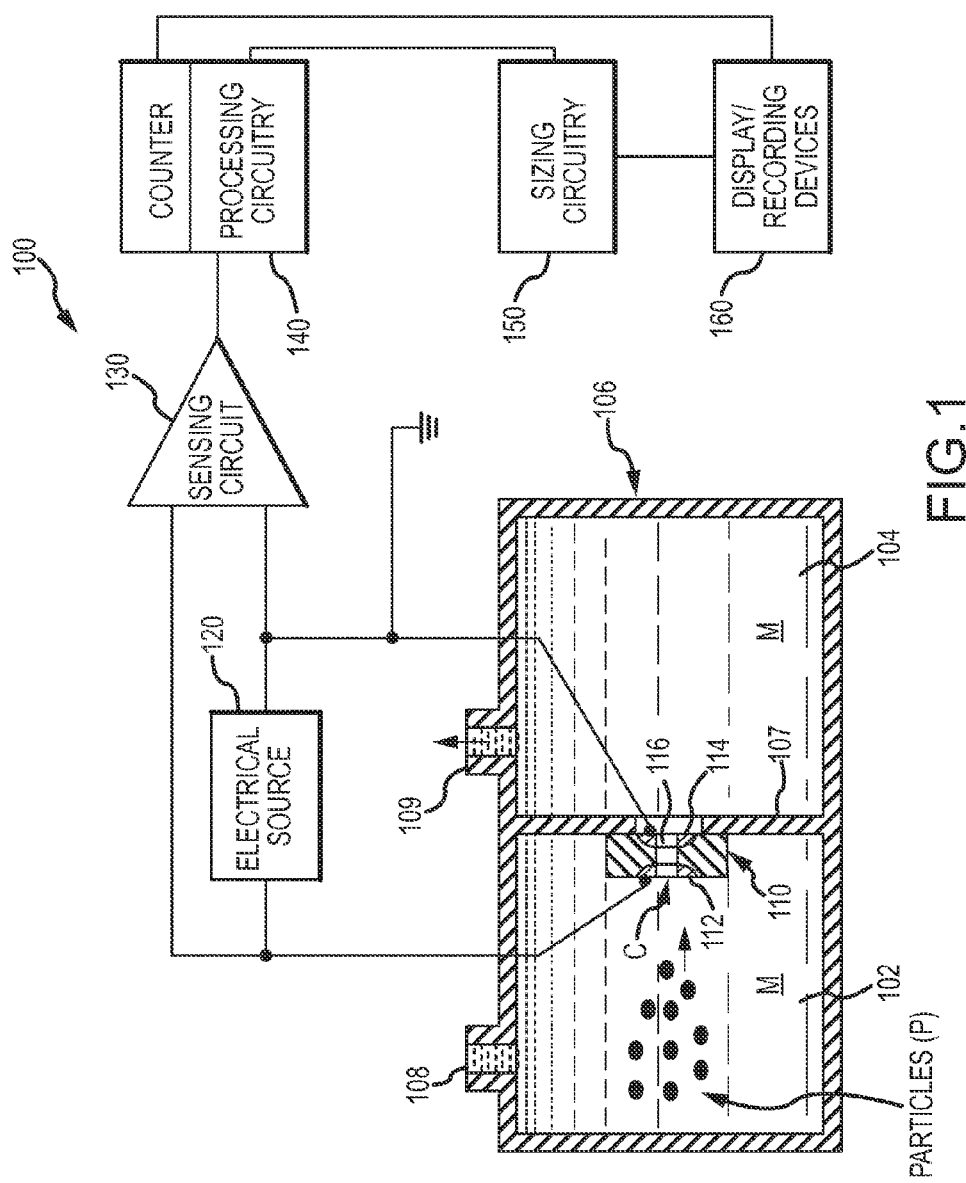
FIG. 1 illustrates aspects of a particle evaluation system according to embodiments of the present invention.

Turning now to the drawings, FIG. 1 depicts aspects of an exemplary particle evaluation system 100 according to embodiments of the present invention. The system 100 can be used for evaluating particles of a biological sample obtained from an individual. As shown here, the system 100 includes a dual-compartment dielectric vessel 106 containing a wall 107 of dielectric material separating compartments 102 and 104, each of which contains a particle-suspending liquid medium M (e.g., isotonic saline solution). System 100 also includes a volumeter assembly 110 having a volumeter conduit C that is adapted to receive a particle-containing fluid suspension therethrough. The volumeter assembly 110 may be coupled with or integral to wall 107. A small through-hole transpiercing volumeter assembly 110 provides a volumeter conduit C which constitutes an operative electrical and fluidic connection between compartments 102 and 104. Hence, a first chamber or compartment 102 can contain a fluid suspension or a portion thereof, and can be in fluid communication with a first orifice (e.g. an opening in assembly 110 facing toward chamber 102). Similarly, a second chamber or compartment 104 can contain a fluid suspension or a portion thereof, and can be in fluid communication with a second orifice (e.g. an opening in assembly 110 facing toward chamber 104).

In operation, an electrical source 120 electrically connected with field amending units 112, 114 establishes an electrical flow through conduit C. For example, where the electrical source is a current source, the source 120 establishes a current flow through conduit C. In some instances, particles (P) can be introduced into compartment 102 via inlet port 108, and a vacuum applied to port 109 can operate to establish or facilitate a flow of suspended particles (P) from compartment 102 through conduit C and into compartment 104. In addition to or as an alternative to the inlet and vacuum port fluid control features shown here, embodiments of the present invention encompass the incorporation of any of a variety of other fluid-control means for facilitating passage of suspended particles (P) through the conduit. Often, operation of a particle evaluation system may involve coordinating the function of a fluid-control means with characteristics of the conduit.

Conduit C may operate to constrict both the electric and hydrodynamic fields so established in vessel 106, so that wall 116 of conduit C surrounds and defines the flows of particle suspension and electric current between compartments 102 and 104. As discussed elsewhere herein, the conduit can provide a wall of hydrodynamic smoothness, having contiguity at the junction of the first and second peripheral conduit walls (e.g. associated with field amending units 112, 114) with the central conduit wall (e.g. of a central substrate disposed between the field amending units). According to some embodiments, the conduit defines an axial conduit wall length having a central region of higher electrical resistivity (e.g. corresponding to the central substrate) disposed between a first distal region (e.g. corresponding to field amending unit 112) of lower electrical resistivity and a second distal region (e.g. corresponding to field amending unit 114) of lower electrical resistivity. Relatedly, according to some embodiments, the central region of the conduit wall length can be provided by a layer of material having high electrical resistivity, and the first and second distal regions of the conduit wall length can be provided by a first layer of material having a lower electrical resistivity and a second layer of material having a lower electrical resistivity, respectively.

According to some embodiments, the conduit can define an axial conduit wall length having a central region disposed between a first peripheral region (e.g. corresponding to field amending unit 112) and a second peripheral region (e.g. corresponding to field amending unit 114), where the central region has an electrical impedance greater than electrical impedances of the first and second peripheral regions. An electrical source 120 can be in operative association with the first and second peripheral regions, and can be configured to provide electrical excitation to the first and second peripheral regions. A sensing circuit 130 can be in operative association with the first and second peripheral regions, and can be configured to detect impedance changes occasioned by particles of the biological sample passing through the first and second peripheral regions.

Figure 3:
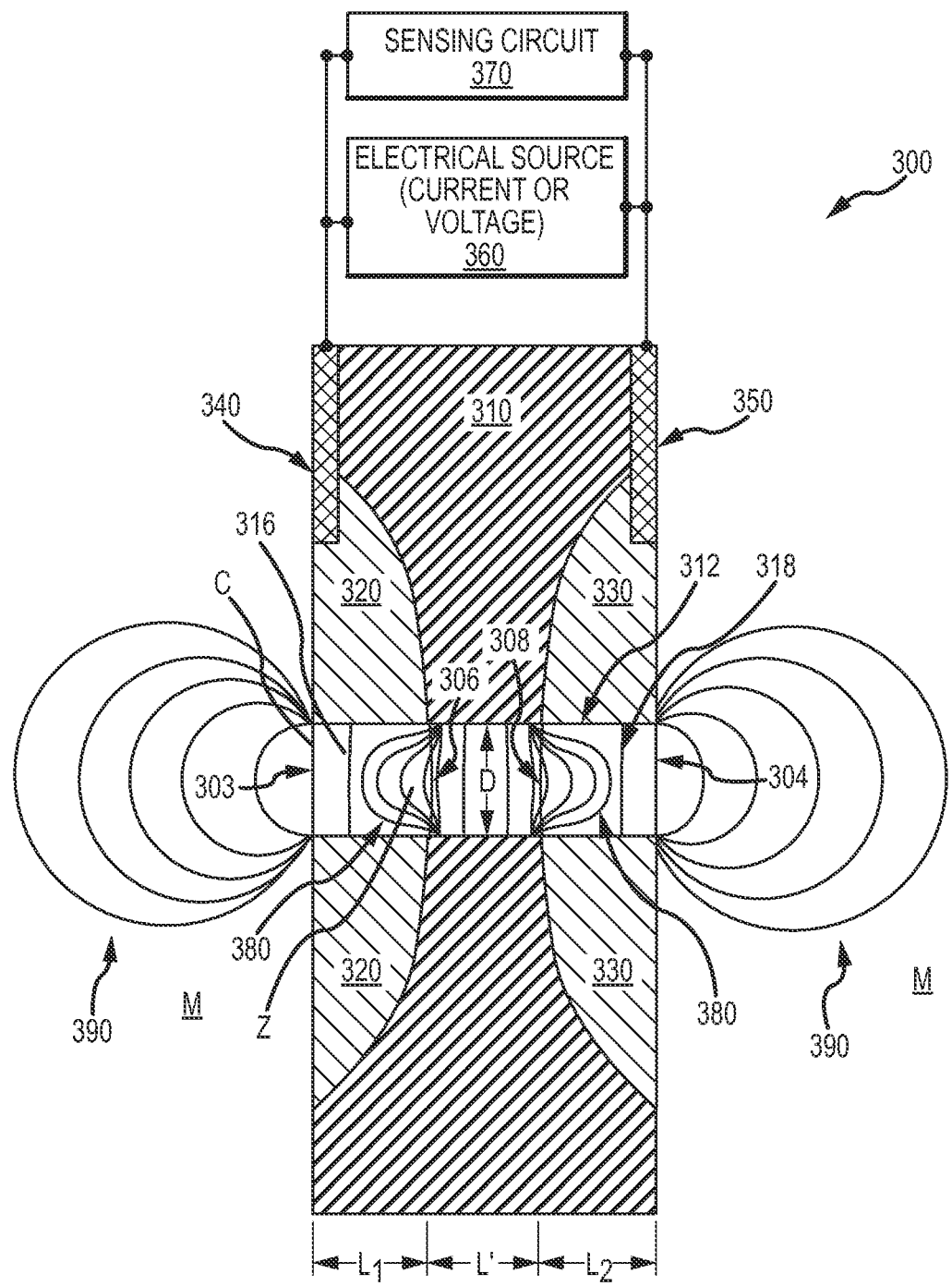
FIG. 3 illustrates aspects of a particle evaluation system according to embodiments of the present invention.

Exemplary methods for evaluating particles of a biological sample obtained from an individual may include transmitting a fluid suspension containing the particles (P) through a volumeter assembly conduit (C). In some cases, the conduit can define an axial conduit wall length having a central region of higher electrical resistivity disposed between a first distal region (e.g. corresponding to field amending unit 112) of lower electrical resistivity and a second distal region (e.g. corresponding to field amending unit 114) of lower electrical resistivity. Methods may also include providing an electrical excitation current to the first and second distal regions with a current source and sensing circuit module (e.g. electrical source 120 in combination with sensing circuit 130) in electrical connectivity with the first and second distal regions, so as to establish a particle-sensitive zone within the conduit (e.g. zone Z as shown in FIG. 3). Further, methods may include detecting current changes occasioned by the particles (P) of the biological sample passing through the particle-sensitive zone with the current source and sensing circuit module via the first and second distal regions.

In some instances, electrical source 120 is a constant-current source such that the current it supplies is substantially independent of changes in impedance between field amending units 112 and 114. In some instances, electrical source 120 is a voltage source having a high internal impedance. In some instances, a sensing circuit 130 can be in operative association with field amending units 112, 114, and can function to detect impedance changes within the conduit C occasioned by particles passing therethrough. Hence, a current source (e.g. source 120) and sensing circuit (e.g. source 130), optionally in combination as a module, can be in electrical connectivity with first and second distal regions of the volumeter assembly, such that the current source and sensing circuit module is configured to provide an electrical excitation current to the first and second distal regions (e.g. corresponding to field amending units 112, 114) to establish a particle-sensitive zone within the conduit, and the current source and sensing circuit module can be configured to detect current changes occasioned by particles of the biological sample passing through the particle-sensitive zone. As shown here, circuitry 130, 140, 150, and 160 can be electrically associated with field amending units. These circuitry components can operate to sense, monitor, process current pulsations in conduit current as occasioned by the more or less individual passage of particles through conduit C, and display evaluation results. For example, the circuitry can include a sensing circuit component 130 such as an AC-coupled sensing circuit, a counter and processing circuitry component 140, a sizing circuitry component 150, and a display or recording component 160. The display or recording component 160 can operate to display or record particle count and characteristic data. In some instances, electrical source 120 is configured to provide a DC current. In some instances, electrical source 120 is configured to provide an AC current. In some instances, electrical source 120 is configured to provide a combination of AC and DC currents. According to certain embodiments, electrical source 120 includes an AC-coupled sensing circuit that has a low input impedance compared to the conduit impedance. With current excitation, it may be desirable to use low-input impedance in a preamp.

Hence, a particle evaluation system provides an exemplary means for detecting, counting, or otherwise analyzing particles whereby a fluid containing such particles is passed through a constricted path within a conduit, and the presence or absence of a particle within the constriction or conduit gives rise to a detectable change in the electrical characteristics of the constricted fluid path. Relatedly, a particle evaluation system provides an exemplary means for detecting, counting, or otherwise analyzing particles whereby a constricted current path is established within a fluid suspension containing particles, and the presence or absence of a particles disposed in the constricted current path can produce detectable changes in the circuit carrying the current.

As discussed elsewhere herein, due at least in part to certain properties of the conduit C, the evaluation apparatus 100 may provide accurate particle characterization results, without using fluidic subsystems such as hydrodynamic flow focusing or sweep flow.

According to some embodiments, a direct current (DC) can be provided through the conduit, and resistive Coulter volume (V) signals can be acquired via the field amending units positioned outside the opposite ends of the volumeter conduit. According to some embodiments, an excitation current including at least one alternating current (AC) can be provided through the conduit, thereby permitting determination of not only the resistive but also reactive components of the conduit current resulting from its modulation by passage of a particle body. When such currents include one having a frequency in the radio-frequency (RF) range (e.g., 22.5 MHz), the respective components permit estimation of the volume (V) and electrical conductivity (C) of a formed body, and the ratio of the reactive to resistive components can said to be the "opacity" of the particle body.

Figure 2:
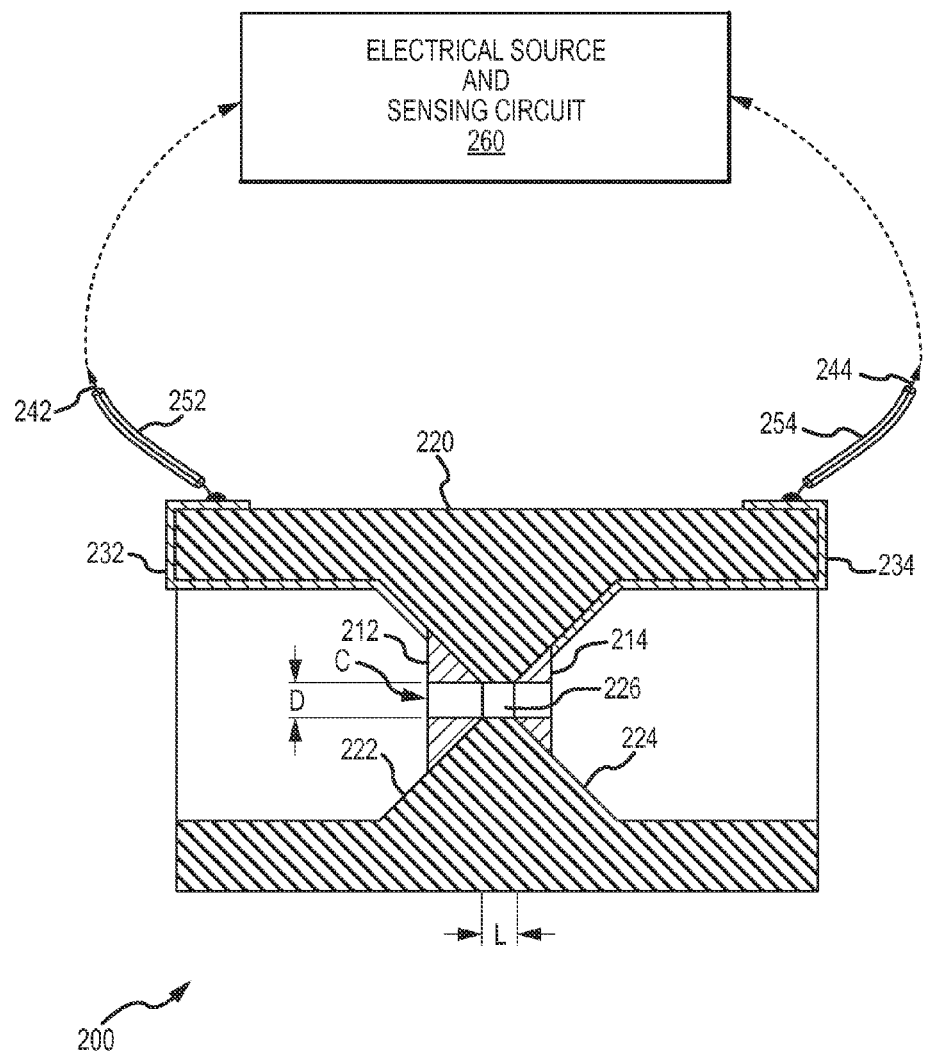
FIG. 2 illustrates aspects of a particle evaluation system according to embodiments of the present invention.

FIG. 2 depicts aspects of a volumeter assembly 200 according to embodiments of the present invention. As discussed elsewhere herein, a volumeter assembly can be part of a particle evaluation system such as that shown in FIG. 1. For example, the volumeter assembly may be disposed between compartments that contain a particle-suspending liquid medium, such that a volumeter conduit C provides an operative electrical and fluidic connection between the compartments. As depicted in FIG. 2, field amending units 212, 214 can be in operative electrical connectivity with an electrical source and sensing circuit module 260, for example via respective conductive connections 232, 234. The electrical source can include a current source or a voltage source. According to the configuration shown here, the field amending units 212, 214 can operate as electrodes for providing electrical excitation to the aperture or conduit C, and can also operate to perform a pulse pickup function when a particle transits the composite volumeter conduit C (e.g. through field amending unit 212, substrate 220, and field amending unit 214).

In some cases, the volumeter assembly 200 can be constructed as a flow cell of the type described in U.S. Pat. No. 3,628,140 or 4,515,274. Such flow cells can be made from an optically transparent material such as fused quartz, synthetic silica, sapphire, or beryllia, and can be used in devices which combine the Coulter principle with optical sensing modalities. Other suitable materials for use in construction of the volumeter assembly are discussed elsewhere herein. Exemplary flow cell embodiments include the devices of U.S. Pat. Nos. 4,791,355, 5,125,737, and 5,616,501. In some instances, evaluation systems as disclosed herein may include fluidic subsystems providing hydrodynamically focused flow. In some instances, particle evaluation systems may not include fluidic subsystems providing hydrodynamically focused flow. In some instances, particle evaluation systems as disclosed herein may include fluidic subsystems providing sweep flow. In some instances, particle evaluation systems may not include fluidic subsystems providing sweep flow. In some instances, particle evaluation systems as disclosed herein may include fluidic subsystems providing hydrodynamically focused flow and sweep flow. U.S. Pat. No. 8,189,187 discusses hydrodynamically focused flow and sweep flow techniques which could be used in conjunction with particle evaluation techniques disclosed herein.

According to certain embodiments, a volumeter conduit C can have a constant circular cross-section, of a diameter D in the 0.030 mm to 0.200 mm range. As shown here, volumeter assembly 200 includes a first field amending unit or collar 212 and a second field amending unit or collar 214. The field amending units 212, 214 also include interior passages or apertures of diameter D, and are adapted into conical cups 222 and 224 in the dielectric flow cell 220. The thicknesses of collars 212 and 214 combine with the length L of functional conduit 226 to form the hydrodynamically smooth conduit C.

In some instances, collars 212, 214, can be made of a platinum alloy or other appropriate material. According to some embodiments, the field amending units or collars 212, 214 can be inset into flow cell 220 so that the outer collar surfaces are smoothly continuous with the conical cups 222 or 224. Elements 212 and 214 can be joined with flow cell 220 using any appropriate method, e.g., use of metal-loaded epoxies or frits, or extensions 232 and 234 which may provide or be part of electrically conductive paths 242 and 244 to respective collars 212 and 214. In other implementations, holes formed through element 220 (and located out of any desired optical path) may be used to provide access for electrically conductive path 242 or 244 to respective field-amending collars 212 or 214. In some cases, a compatible conductive epoxy may be used to both establish and protect the electrical junction. For example, the conductive paths 242 and 244 to respective elements 212 and 214 can be coated with epoxy or insulating elements 252 and 254. Accordingly, the conductive paths can be protected from any degrading influence of a suspending medium or other deleterious factors. As shown here, conductive connections 232, 234 can also be in operative electrical connectivity with a current source and sensing circuit module 260.

In some embodiments, volumeter assemblies may provide conduits of prismatic cross section, for example such as those as discussed in U.S. Pat. No. 4,348,107, by incorporating appropriate collars of minimal thickness at least approximating the diagonal of the particular conduit cross section and providing operative electrical connections thereto. In some instances, conduits of square cross section may be implemented in particle evaluation systems. Hydrodynamically focused flow may be used with field-amending volumeter conduits, e.g., to stabilize suspension flow through the sensitive zone. As discussed elsewhere herein, a particle evaluation system may operate without using hydrodynamically focused flow. In some cases, the length L, the entry shape of collar 212, or other parameters of the volumeter conduit may be selected so that acceptable performance can be achieved without use of hydrodynamically focused flow.

As discussed elsewhere herein, the conduit C can provide a wall of hydrodynamic smoothness, having contiguity at the junction of the first and second peripheral conduit walls (e.g. associated with field amending units 212, 214) with the central conduit wall (e.g. of a central substrate 220 disposed between the field amending units. The conduit C can operate to receive suspended particles therethrough, and can define a central wall region (e.g. provided by substrate 220) disposed between a first peripheral wall region (e.g. provided by field amending unit 212) and a second peripheral wall region (e.g. provided by field amending unit 214). The central wall region typically has an electrical impedance greater than electrical impedances of the first and second peripheral wall regions. In operation, the electrical source provides electrical excitation to the first and second peripheral regions, and the sensing circuit, which is also coupled with the first and second peripheral regions, detects impedance changes within the conduit occasioned by particles passing therethrough.

FIG. 3 shows aspects of a volumeter assembly 300, according to embodiments of the present invention. Here, a conduit C is provided by a substrate 310 and field amending units 320, 330. As shown here, the field amending units 320, 330, can operate to establish internal e-field equipotentials 380 associated with the interior of the conduit, and external e-field equipotentials 390 associated with the exterior of the conduit. In some instances, the substrate 310 is made of sapphire, although other materials may be used for fabrication of the substrate as discussed elsewhere herein. The volumeter assembly may also include electrodes or conductive connections 340, 350 in operative association or electrical connectivity with field amending units 320, 330, respectively. The conductive connections 340, 350 or other electrical circuitry associated therewith can be produced using integrated circuit techniques. In some cases, conductive connections can be placed on the substrate using techniques such as those described in U.S. Pat. No. 4,760,328.

As shown here, the field amending units 320, 330 can be in operative electrical connectivity with an electrical source 360 and sensing circuit 370. In some embodiments, the electrical source and sensing circuit can be provided as separate modules. In some embodiments, the electrical source and sensing circuit can be combined in a single module. In some embodiments, the electrical source and sensing circuit can be electronically coupled with the field amending units via respective conductive connections 340, 350. The electrical source may include a current source or a voltage source. As shown here, the conduit C can provide a wall of hydrodynamic smoothness, having contiguity at the junction of the first and second peripheral conduit walls (e.g. associated with field amending units 320, 330) with the central conduit wall (e.g. of a central substrate 310 disposed between the field amending units). The conduit C can operate to receive suspended particles therethrough, and can define a central wall region (e.g. provided by substrate 310) disposed between a first peripheral wall region (e.g. provided by field amending unit 320) and a second peripheral wall region (e.g. provided by field amending unit 330). The central wall region typically has an electrical impedance greater than electrical impedances of the first and second peripheral wall regions. In operation, the electrical source provides electrical excitation to the first and second peripheral regions, and the sensing circuit, which is also coupled with the first and second peripheral regions, detects impedance changes within the conduit occasioned by particles passing therethrough. Based on this design, it is possible to operate the device using low current or power. Operation of the device may also avoid or reduce the generation of high field gradients near an interface between a peripheral conductive field amending unit and the central insulative substrate, which in turn can eliminate or reduce the generation of gas bubbles due to electrolysis caused by current densities, and hence can improve the detection or sizing of particles passing through the conduit (e.g. without undue interference from such gas bubbles). In some instances, an external field caused by a field amending unit (e.g. in the absence of inhibition provided by an external excitation) is sufficiently weak that it does not unduly affect performance of the device.

According to some embodiments, an external field can originate from potentials applied to the field-amending elements and/or from external electrodes remote from them. If both fields are present, as in the case of a four-terminal potential-sensing configuration, the external field can be the result of superposition of the two, but with lessening impact the further from the conduit. In some cases, external fields caused by remote excitation electrodes can be distributed differently due to the conductive field amending units on a conduit substrate.

According to some embodiments, equipotentials are only part of an orthogonal network originating at right angles to insulative surfaces and more or less parallel to conductive ones, and another part of the network (not shown in FIG. 3) may include the current trajectories which intersect the equipotentials at right angles.

According to certain embodiments, the substrate or separating layer 310 of volumeter assembly 300 includes a solid material of resistivity substantially greater than that of the suspending medium M in which the particles to be characterized are suspended. As shown here, the substrate 310 can include an inner aperture of diameter D that is smoothly contiguous and unitary with inner apertures of respective axially-distal layers or elements 320 and 330. The distal layers or field amending elements 320, 330 can include uninsulated solid material of resistivity substantially less than that of suspending medium M.

In some cases, conduit C provides a continuous wall 312 defining a right cylindrical conduit of circular cross-section through volumeter assembly 300. For example, wall 312 can be a bore-wall and the conduit cross-section is constant along the axis. In some cases, prismatic or non-constant conduit cross-sections may be used. As shown here, conduit C includes an entry orifice or edge 303 and an exit orifice or edge 304. As discussed elsewhere herein, by delivering electrical excitation to field amending units that are at the conduit, it is possible to operate a particle evaluation system using less power than what might otherwise be needed when delivering electrical excitation to electrodes disposed at a remote distance from the conduit. The use of lower current to the excited field amended units, for example, can also result in a reduced amount of electrolytic bubble formation at the edges 303, 304.

Conduit C can be defined by a continuous, hydrodynamically smooth wall 312 collectively including sequential wall portions through elements 320, 310, and 330, such that contiguous complementary surfaces of elements 320 and 310 form hydrodynamically smooth delimiting boundary 316, and those of 310 and 330 form hydrodynamically smooth delimiting boundary 318, respectively, between the portions of conduit C bounded by the respective elements 320, 310, and 330.

Accordingly, wall portions of conduit C can thus be circumferentially bounded by an uninsulated solid material composing the respective elements and smoothly contiguous at delimiting boundaries 316 and 318, respectively, to a congruent adjacent wall portion. Consequently, the characteristic electrical resistivity of defining wall 312 can be caused to be substantially axisymmetric, and in some embodiments can be made to have significant axial gradients at delimiting boundaries 316 and 318 along the length of any longitudinal section of conduit C. The characterizing axial variation in axisymmetric resistivities may originate in the characteristics of the solid materials selected for the makeup of volumeter assembly 300, although geometries of individual elements may be caused to augment certain properties of conduit C. Volumeter assemblies incorporating the characteristic axial variation in axisymmetric resistivity of wall 312 may be embodied by a variety of techniques in a broad range of designs, geometries, and materials.

In some instances, the field amending distal elements 320 and 330 assume individual potentials over their surfaces which directly superimpose independent equipotentials in the vicinity of conduit C. For example, the field amending units 320, 330 can operate to establish e-field equipotentials, both inside and outside of the conduit, which depend on the potential between the field amending units, such that both parts of the e-field scale with the potential. In some instances, the distribution of a resultant hydrodynamic through-field depends at least in part on D and the cumulative length ($L'+L_1+L_2$) of conduit C, where $L_1$ and $L_2$ are the dimensions along wall 312 of elements 320 and 330, respectively, and L' is the dimension along wall 312 of element 310.

It is understood that certain features of FIG. 3 are intended to provide an illustrative example, and that certain features may vary in practice. For example, the equipotentials coming off the edges of element 310 may become concentric to the conduit axis, i.e., parallel to the conduit surfaces of 320 and 330, so that not all originate at the outer edge of those two elements. Relatedly, the equipotentials may be extended continuously outward from the edges of 310 into the space outside 320 and 330, with only the weakest equipotentials seeming to originate at the orifices of the conduit portions.

The e-field distribution is typically determined by the shape of the field-amending elements 320 and 330 and the potential difference between them. It is noted that where a voltage source is used, such a source can make the sensed particle pulse sensitive to both electrolyte conductivity and its resistivity change with ambient temperature. As discussed elsewhere herein, the e-field equipotentials, both inside and outside the conduit, typically depend on the potential between the field-amending elements 320 and 330, that is, both parts of the e-field scale with the potential.

In the two-terminal embodiment depicted in FIG. 3, there is no e-field imposed by remote electrodes. Rather, this drawing indicates that potential can be independently applied to the field-amending elements. As discussed elsewhere herein, particles are typically characterized according to the internal conduit fields 380. The equipotentials 390 external to the field amending unit outer surfaces typically have relatively low potentials, and thus these external fields may be so minimal as to provide little or no contribution to the particle characterization process. During operation, the external e-fields of the field amending units can operate to lengthen an initial and a final near-baseline phase of a sigmoidal rise and fall of particle pulses (e.g. when considering detected current as a function of particle position, as the particle transits the conduit). Typically, these leading and trailing pulse edges are below threshold levels and can be mitigated by DC-restoration methods. For homogeneous surrounding electrolyte in the absence of other applied e-fields, the e-field equipotentials established by field-amending elements 320 and 330 can be almost totally determined by their geometry and potential and so can be nearly independent of whether driven by a current or voltage source. In some instances, the bulging external equipotentials 390 due to the field amending units can have voltages at single digit percentages of the voltage applied, and such low voltages can be below typical sensing levels, and can cause a slowly rising and falling initial and final pulse phases, respectively.

According to certain embodiments, due to their immersion in the particle-suspending liquid medium surrounding volumeter assembly 300 and filling conduit C, field amending distal elements 320 and 330 of volumeter assembly 300 may assume individual potentials over their surfaces which impose new field distributions in the axisymmetric electric field established by current through the conduit. For axial lengths $L_1$ or $L_2$ of elements 320 or 330 greater than approximately the conduit diameter D, the resultant electric field external to conduit C is substantially homogeneous.

As shown here, internal ambit fields or equipotential field regions 380 can operate to provide a particle sensitive zone Z that is within volumeter conduit C. The distribution of the resultant electric field making up sensitive zone Z may depend at least in part on conduit diameter D at boundaries 306 (e.g. within conduit and defined between field amending unit 320 and substrate 310) and 308 (e.g. within conduit and defined between substrate 310 and field amending unit 330) and axial length L' of conduit portion 370, while the semielliptical equipotentials corresponding to a desired detectability threshold may operate to at least in part determine the effective spatial extent of ambit fields 380.

According to certain embodiments, conduit C provides an axial variation in axisymmetric wall resistivity. Further, in certain embodiments, conduit C is fluidically continuous and hydrodynamically smooth throughout its length. In some cases, element 310 has an electrical resistivity substantially greater than that of the particle-suspending medium M and is can be made from a dielectric such as ruby, sapphire, alumina, beryllia, synthetic quartz, or other material suited to a given application. In some cases, element 310 may be made from a lossy dielectric such as a conductive glass, a conductive ceramic, or a type of conductive polymer or plastic, the resistivity of which is effectively greater than that of the suspending medium but less than that of the aforementioned dielectrics. In some cases, elements 320 and 330 have resistivities substantially less than that of the suspending medium M. In some cases, elements 320 and 330 can be made from metals or alloys from the platinum group or conductive ceramics such as certain titanium, tungsten, or silicon carbides. Some applications may benefit from use of metals such as gold, silver, titanium tantalum, tungsten, or their various alloys. Still other applications may benefit from use of nickel, copper, or their alloys, either as a metal or as a cermet comprising one of these metals infiltrated into the microstructure of a ceramic such as alumina. Yet other applications may benefit from use of glassy carbon. Elements 320 and 330 need not be of the same material, and some applications of the volumeter assembly may benefit from a judicious mismatch in one or more material properties. In some cases, the materials may be homogeneous. In some cases, the materials may be inhomogeneous. In some cases, elements 320 or 330 may be formed from one material and coated or plated with another material in order to provide combinations of material properties. In some cases, high-resistivity element 310 is formed of alumina of appropriate grain size and purity, and elements 320 and 330 are made of an appropriate cermet (e.g., alumina infiltrated with nickel or other metal appropriate to the intended application)

or one of the conductive ceramics (e.g., titanium carbide). Complementary elements 310, 320, and 330 may be molded (e.g., by injection processes), sintered, finished to form if desired, and joined (e.g., by appropriate brazing methods or through use of appropriate metal-filled adhesives) prior to transpiercing and finishing volumeter assembly 310 to the desired conduit diameter D' and lengths $L_1$ and $L_2$.

In some embodiments, elements 320 and 330 of volumeter assembly 300 may be either preformed of one of the metallic conductors and appropriately affixed into concavities in element 310 or formed in place therein, e.g., through use of an appropriate metallic-filled adhesive or paint. For example, discs of 1.0 mm thickness may be prepared from a convenient rod of 99.5% purity alumina having grain size in the range between 0.003 mm and 0.005 mm, and centered spherical concavities approximately 0.40 mm deep by 1.0 mm in segment diameter at the surface of the disc are prepared on each side of the discs. In some embodiments, concavities in element 310 may be either filled with gold-filled adhesive and cured, or given repeated coats of a platinum-filled paint such as used in forming electrodes on glass and fired, according to the appropriate protocol to form a slightly protruding conductive deposit in each concavity. Each disc may then be lapped flat on each surface to form elements 320 and 330, transpierced through the center of the disc, and the through-holes finished to form hydrodynamically smooth circular conduit C. In some embodiments, element 310 of a volumeter conduit may include a lossy ceramic. In some embodiments, a volumeter assembly 300 may be constructed from a single material, by using suitable doping methods to induce an appropriate resistivity profile. At the site intended for forming the through-hole defining field-amending conduit C, the electrical resistivity of an appropriate solid substrate may be made to effectively vary through the thickness thereof, e.g., to define a central delimited region of high electrical resistivity (approximately equal in thickness to the intended conduit diameter) which is contiguously bounded by distal regions of substantially lesser electrical resistivity (approximately equal in thickness to one to three times the intended conduit diameter). For example, suitable semiconductor impurity doping methods may be used to create regions 320 and 330 of substantially lesser resistivity which intersect the surfaces on opposite sides of an intrinsic semiconductor (e.g., silicon) substrate 310 to form exposed regions of diameter approximately five times the conduit diameter. The exposed surfaces of regions 320 and 330 may be electrically uninsulated, and all exposed surfaces of volumeter assembly 300 may be made to be compatible with the liquid medium used to suspend the particles.

According to some embodiments, the field amending units 320, 330 and the respective conductive connections 340, 350 may be constructed of the same material. In some instances, a combined field amending unit and conductive connection (e.g. elements 320 and 340) can be provided as a single unitary structure. As discussed elsewhere herein, the field amending units can operate to shape the ambit fields of the conduit or aperture. Relatedly, currents between electrodes or conductive connections near the field amending units can also affect the ambit fields (e.g. fields 301 and 302).

As shown here, where the field amending units are configured to function as aperture excitation electrodes, the allowable aperture excitation current can be significantly reduced. Because low aperture excitation currents can be effectively employed, exemplary particle evaluation volumeter assemblies (e.g. two terminal configurations) are well suited for use in producing a Coulter Counter on a chip, with or without actual single-chip implementation of the aperture and electronics. For example, the power requirements involved with effectively exciting such volumeter conduits can be significantly reduced compared with other known aperture based sensing systems. By incorporating the use of lower excitation currents, it is possible to implement particle evaluation systems with more integrated components and smaller hybrid components.

In a four-terminal configuration, the shape of the electrode or conductive connection may have a more significant effect where the electrode or conductive connection is positioned more closely to the conduit or aperture. Depending on any impedance operatively connected to the conductive connections 340, 350, the contact between the conductive connections 340, 350 and the corresponding field amending units 320, 330 may affect the surface potentials of the field amending units. Hence, in some embodiments, the field amending units and conductive connections may be free of connections to any other external circuitry, other than that associated with the current source and sensing circuit.

Figure 4:
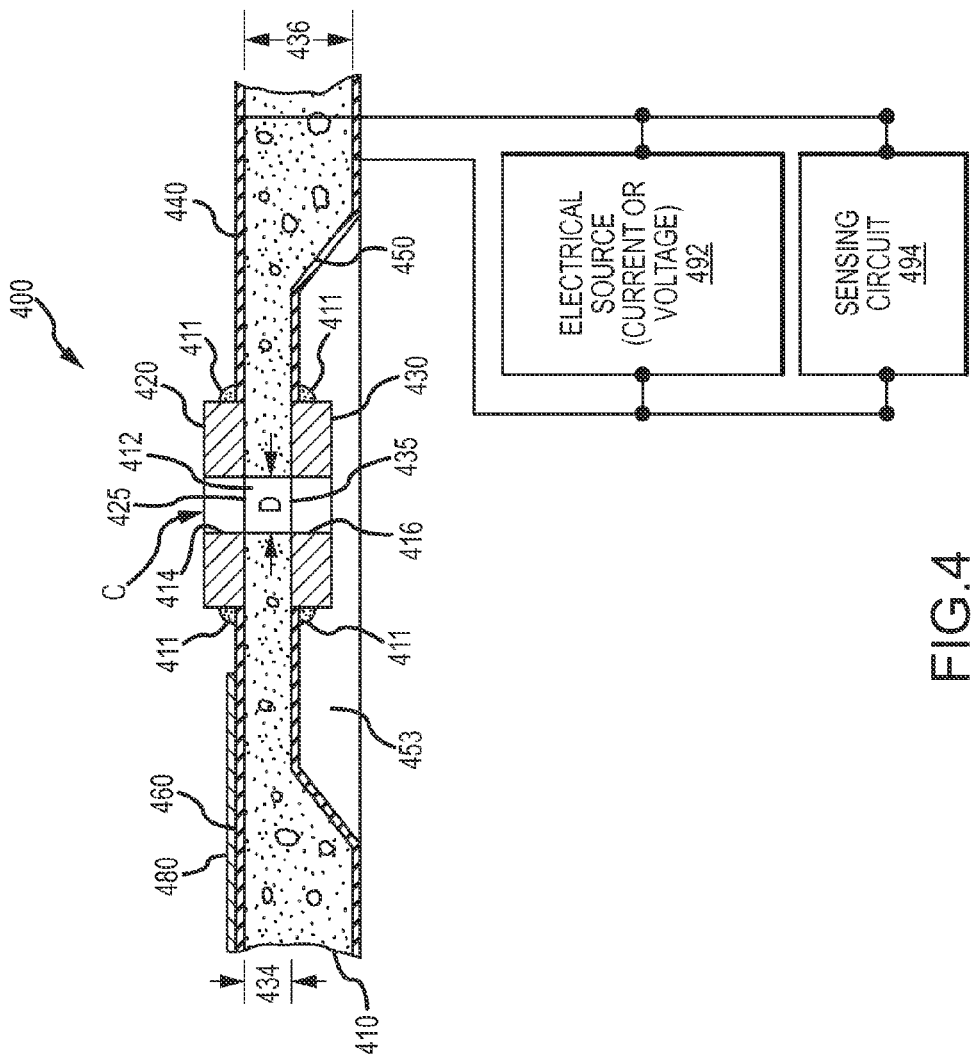
FIG. 4 illustrates aspects of a particle evaluation system according to embodiments of the present invention.

FIG. 4 illustrates aspects of a volumeter assembly 400 of a particle evaluation system, according to embodiments of the present invention. Volumeter assembly includes a substrate 410, and first and second field amending units 420, 430. As shown here, the first field amending unit 420 is operatively connected with a first electrode or conductive connection 440, and the second field amending unit 430 is operatively connected with a second electrode or conductive connection 450. Conductive connections 440, 450 are in electrical connectivity with other circuitry, such that the field amending units 420, 430 can operate to facilitate the sensing of electrical fluctuations within conduit C or circuitry associated with the field amending units.

During a particle evaluation process or method, where electrical excitation is provided at the conduit via the field amending units 420, 430, a particle transiting through conduit C can operate to raise change the resistivity within the confines of the substrate wall 412. For example, the particle may increase the resistance inside of the conduit. Accordingly, where a current source is used, excitation current provided by a field amending unit which would otherwise pass through the conduit in the absence of such a particle or increased resistivity consequently may be diverted either back into the excitation source (e.g. electrical source 492) or into the sensing circuitry (e.g. circuit 494) depending on the relative impedance of the excitation source and sensing circuit. For example, with a low-impedance sensing circuit, the current can be diverted into such a sensing circuit and sensed therein as a current pulse. Where the excitation source 492 is a voltage source, a particle transiting through conduit C can operate to produce a voltage pulse. Hence, in some instances evaluation of a particle may involve sensing pulsations in current, and in some instances evaluation of a particle may involve sensing pulsations in voltage.

In this sense, the volumeter assembly may facilitate a two-terminal current sensing Coulter approach for analyzing particles. For example, as shown here, the field amending units 420, 430 can be in operative electrical connectivity with a current source and sensing circuit module, for example via respective conductive connections 440, 450. Relatedly, the volumeter assembly may facilitate a two-terminal potential sensing Coulter approach for analyzing particles. For example, as shown here, the field amending units 420, 430 can be in operative electrical connectivity with a voltage source and sensing circuit module, for example via respective conductive connections 440, 450. Such configurations can allow the volumeter assembly to operate in the absence or minimized presence of a hydrodynamically focused flow for guiding particles through the conduit. These constructions can also allow such volumeter assemblies to operate in the absence or minimized presence of a sweep flow for moving particles once they have passed through the conduit. According to some embodiments, the field amending conductive collars at the conduit inlet and outlet orifices can operate to contain the orifice electric fields therewithin, and thus the coincidence volume of the conduit can be reduced.

The conduit C can provide a wall of hydrodynamic smoothness, having contiguity at the junction of the first and second peripheral conduit walls (e.g. associated with field amending units 420, 430) with the central conduit wall (e.g. of central substrate 410 disposed between the field amending units). The conduit C can operate to receive suspended particles therethrough, and can define a central wall region (e.g. provided by substrate 410) disposed between a first peripheral wall region (e.g. provided by field amending unit 420) and a second peripheral wall region (e.g. provided by field amending unit 430). The central wall region typically has an electrical impedance greater than electrical impedances of the first and second peripheral wall regions. In operation, the electrical source provides electrical excitation to the first and second peripheral regions, and the sensing circuit, which is also coupled with the first and second peripheral regions, detects impedance changes within the conduit occasioned by particles passing therethrough.

As depicted in FIG. 4, the field amending units 420, 430 are contiguous with the respective conductive leads 440, 450. Conduit C is defined by a substrate wall 412, and coaxially aligned congruent wall portions 414 and 416 of the field amending units 420, 430, respectively. The uninsulated elements 420, 430 may be operatively connected with respective electrodes or conductive connections 440, 450 by an appropriate conductive bond 411, such as a conductive epoxy or a low-temperature solder. Hence, conduit C can be defined by a continuous, hydrodynamically smooth wall that collectively includes sequential wall portions 414, 412, and 416, through elements 420, 410, and 430 of the volumeter assembly 400. The contiguous complementary surfaces of elements 420 and 410 form a hydrodynamically smooth delimiting boundary 425, and the contiguous complementary surfaces of elements 410 and 430 form a hydrodynamically smooth delimiting boundary 435, respectively, between the portions of conduit C bounded by the respective elements 420, 410, and 430. Thus, the individual wall portions (414, 410, and 416) of conduit C are circumferentially bounded by the uninsulated solid material composing the respective elements (420, 410, and 430) and smoothly contiguous at boundaries 425 and 435, respectively, to a congruent adjacent wall portion.

According to certain embodiments, the electrical resistivity of element 410 is substantially greater, and the electrical resistivity of elements 420, 430 less, than that of the liquid in which the particles to be characterized are suspended. Consequently, the characteristic electrical resistivity of the composite wall defining conduit C can be substantially axisymmetric, and can have significant axial gradients at delimiting boundaries 425 and 435 along the length of any longitudinal section of conduit C. The characterizing axial variation in axisymmetric resistivities may substantially originate in the characteristics of the solid materials selected for the make-up of the volumeter assembly. In certain embodiments, the geometries of individual elements (e.g. 420, 410, and 430) may operate to augment certain properties of the conduit C. Volumeter assemblies incorporating the characteristic axial variation in axisymmetric resistivity of the wall may be embodied by a variety of techniques in a broad range of designs, geometries, and materials.

In some embodiments, element 410 can be made of semiconductor-grade sapphire (e.g. of the type used in silicon-on-sapphire integrated-circuit technology) polished to thickness 436. Such sapphire substrates may be available in standard thicknesses of 0.125 mm and 0.250 mm, for example. Elements 420 and 430 may be provided as uninsulated collars formed of an electrically conductive material (e.g., a platinum alloy or titanium carbide), and fixed to element 410 so that the respective congruent through-holes defining walls 414, 412, or 416 in the three elements 420, 410, and 430 align to form a fluidically continuous and hydrodynamically smooth wall.

As shown here, within individual device regions on such substrates, there may be provided a recess 453 into a first surface (the lower surface shown in FIG. 4), of depth and diameter appropriate to the diameter D and length 434 of the conduit C provided therein. According to some embodiments, the recess 453 can operate to locate element 430 in its approximate position. In some instances, recess 453 may be etched as part of a circuit-fabrication process whereby integrated circuitry 460 is formed, although recess 453 may be formed by other means. The formation of integrated circuitry 460 on substrate 410 may be made by other processes as well. An exemplary integrated-circuit technique may involve using sequential photolithographic projections through patterned masks, followed by development and processing of the prepared surface area. According to some embodiments, an epitaxial silicon layer can be formed in a desired pattern on a surface of substrate 410, and integrated circuitry 460 can be formed therein, according to integrated-circuit techniques. In some instances, circuitry 460 may include a low-noise amplifier circuit, to allow coupling of the low-level current pulsations occasioned by particles transiting conduit C to be relayed to remote signal-processing circuitry. In some instances, circuitry 460 may include other types of circuits, such as those that may otherwise be provided as printed circuit cards in a cabineted apparatus. Interconnects between such sub-circuits, as well as conductive paths used for input/output and power connections, can also be provided. These may be formed by converting epitaxial intrinsic silicon to a more conductive form in the desired pattern, for example, or by conversion to polysilicon (e.g. electrode or conductive lead 440), by doping with donor impurities, or by application of metalization layers in the desired pattern.

In some embodiments, a conductive guard layer 480 can be formed over the completed integrated circuit and conductive paths, and insulated from them. For some applications it may be desirable to protect the entire second surface (the upper surface shown in FIG. 4), except for the terminations of the output and power paths and electrode 440, by a layer of inert dielectric such as silicon dioxide. Electrode or conductive lead 440 can then be formed by metalizing a desired pattern on the first surface of the substrate. The individual device chips can then be separated in a dicing operation and tested for electrical function. The outer dimensions may be chosen for handling convenience. According to some embodiments, individual devices in the range of 4 to 6 mm may be used. Where a round device chip is desired, the chips may be separated by etching methods, for example.

In some instances, an undersized through-hole can be formed by photo ablation in each device chip at the desired location of conduit C, and field-amending elements 420 and 430 (having undersized respective openings 414 or 416) can be aligned and positioned over each rough conduit, e.g., with an alignment wire as described in U.S. Pat. No. 6,111,398, and appropriately attached to the respective surfaces of 410. The undersized conduit C can then be finished to a desired diameter D by polishing according to Coulter wafer processing techniques. Operative electrical connections between field-amending elements 420 and 430 and respective conductive leads 440 and 450, and between appropriate external connectives and the terminations of the output and power paths, can be formed using various techniques, such as with a conductive epoxy paint or epoxy or a low-temperature solder. In certain embodiments, electrical connections can be protected from corrosion by a layer of insulative material. With some materials it may be desirable to mount disc preforms of 420 and 430, photo ablate the rough conduit through the conjoined assembly, and then polish the conduit to the desired diameter D. This process sequence may involve attaching field amending preforms to substrate 410 prior to separating the device chips and can avoid the step of aligning elements 420 and 430 over the rough conduit openings to the required degree. With other materials, the disc preforms may be provided an undersized opening, attached to substrate 410, conduit C enlarged and cleared by photo ablation, and then finished by polishing to the final diameter D. The device chips may then be tested for electrical function and provided practical furniture, such as electrical connections and a mount and protective means suited to the intended application. The completed devices may then be functionally tested, calibrated, and provided the appropriate identification means. Depending on intended application, many forms of the apparatus are possible.

Figure 5:
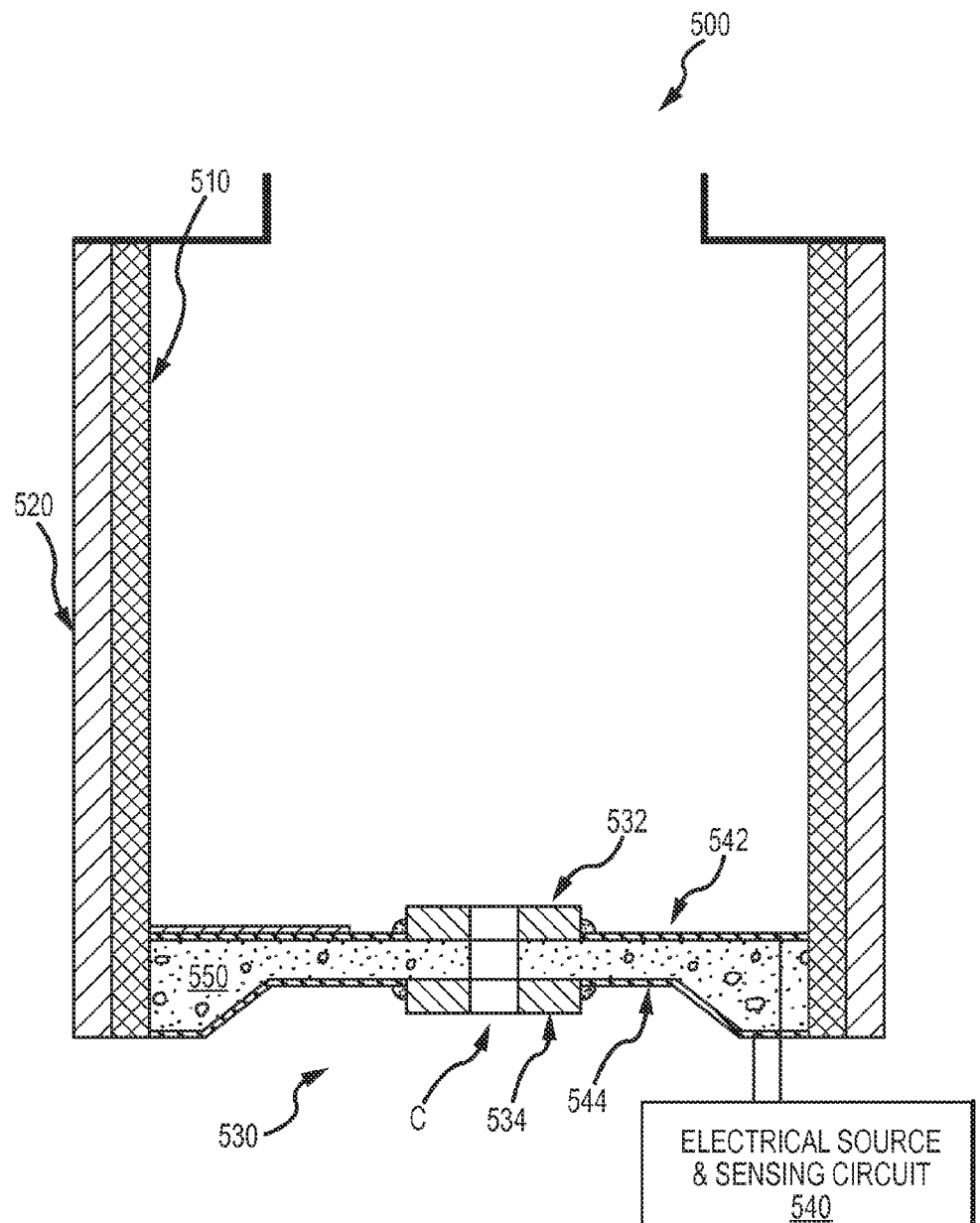
FIG. 5 illustrates aspects of a particle evaluation system according to embodiments of the present invention.

FIG. 5 illustrates aspects of a particle evaluation system 500, according to embodiments of the present invention. As shown here, the system includes a tubular ceramic element 510, which may be housed under slight compressive strain in a metal tubular sleeve 520 and containing an internal flow channel in fluid communication with conduit C. In some instances, a particle evaluation system may include an appropriate electrical connector operatively connected to a volumeter assembly 530 and appropriate pipe fittings, so as to be substantially continuous with a process line to be monitored. Such a particle detection device may have wide applicability. For example, inserted into a process line having appropriate flow volumes (such as a pressure line in a hydraulic system) and driven by the appropriate electrical source (e.g. AC current), the device can be used for the detection and Coulter sizing of metallic wear particles accumulating within the process system. For example, embodiments of the device can be used to remotely sense wear-particles in a hydraulic system. In some instances, the process system may be industrial or vehicular, such as an aviation control system. Accordingly, particle evaluation systems as disclosed herein can be used to analyze any of a variety of industrial particles.

In some embodiments, a particle evaluation system may include the tubular ceramic element 510, but not the metal tubular sleeve 520. Such configurations may be well suited for situations where particle evaluation system 500 can be provided an external Faraday shield by a portion of the process being monitored. In some instances, a form without the metal tubular sleeve may be broadly applicable, for example to add particle-sensing capability to low-pressure instrumentation for solute analysis. In some embodiments, the tubular sleeve 520 may be provided on the inside of the tubular ceramic element 510, instead of on the outside as depicted in FIG. 5.

In some embodiments, the particle evaluation system can be used to provide enhanced volumetric accuracy. In some embodiments, the particle evaluation system 500 may include remote signal conditioning circuitry such as that which is described in U.S. Pat. No. 4,760,328. In some cases, circuitry may include an impedance matching amplifier. In some cases, a particle evaluation system may include a baseline restorer or additional circuitry. As shown here, an excitation current source and sensing circuitry 540 can be operatively connected with field amending units 532, 534, optionally via respective conductive leads 542, 544. In a four-terminal configuration, a pair of excitation electrodes can be positioned remotely from the field amending units and operatively connected with an excitation current source, as describe in U.S. Pat. No. 6,175,227.

In some embodiments, tubular sleeve 520 can serve as a common (ground) lead from field amending unit 534 and conductive lead 544 to circuitry 540. As noted above, the metal tubular sleeve 520 may be disposed interior to the tubular element 510, and the tubular element 510 can be fabricated of glass instead of ceramic. In such configurations, the metal tubular sleeve 520 can served both as a Faraday shield and as connection to field amending unit 532 and/or conductive lead 542. The conduit C can provide a wall of hydrodynamic smoothness, having contiguity at the junction of the first and second peripheral conduit walls (e.g. associated with field amending units 532, 534) with the central conduit wall (e.g. of a central substrate disposed between the field amending units. The conduit C can operate to receive suspended particles therethrough, and can define a central wall region (e.g. provided by substrate 550) disposed between a first peripheral wall region (e.g. provided by field amending unit 532) and a second peripheral wall region (e.g. provided by field amending unit 534). The central wall region typically has an electrical impedance greater than electrical impedances of the first and second peripheral wall regions. In operation, the electrical source provides electrical excitation to the first and second peripheral regions, and the sensing circuit, which is also coupled with the first and second peripheral regions, detects impedance changes within the conduit occasioned by particles passing therethrough.

Figure 6:
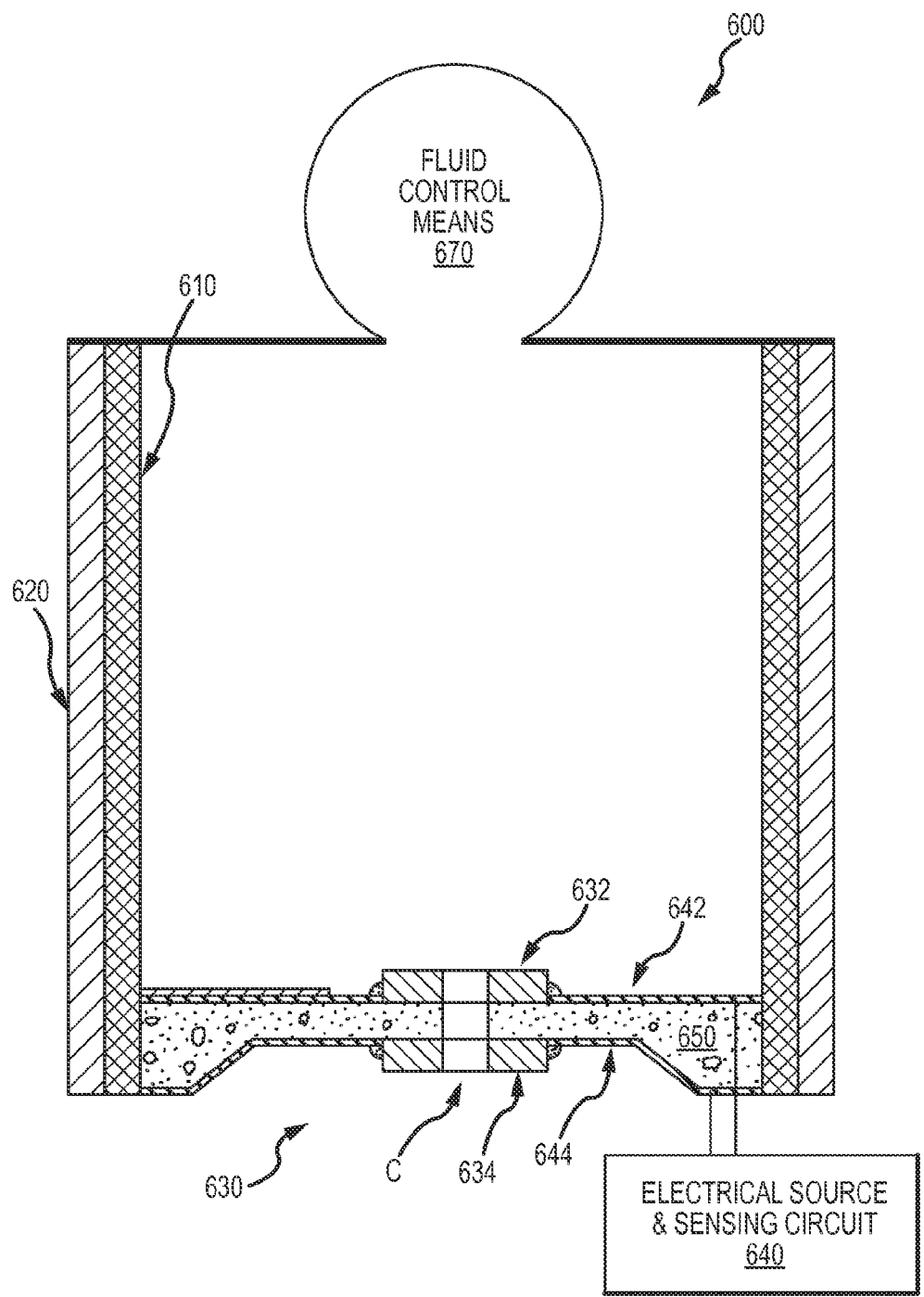
FIG. 6 illustrates aspects of a particle evaluation system according to embodiments of the present invention.

FIG. 6 illustrates aspects of a particle evaluation system 600, according to embodiments of the present invention. As shown here, the system includes a tubular ceramic element 610, which may be housed under slight compressive strain in a metal tubular sleeve 620 and containing an internal flow channel adapted to conduit C. In some instances, a particle evaluation system may include an appropriate electrical connector operatively connected to a volumeter assembly. Such a particle detection device may have wide applicability.

In some embodiments, a particle evaluation system may include the tubular ceramic element 610, but not the metal tubular sleeve 620. In some instances, a form without the metal tubular sleeve may be broadly applicable, for example to add particle-sensing capability to low-pressure instrumentation for solute analysis. In some embodiments, the particle evaluation system can be used to provide enhanced volumetric accuracy. In some embodiments, the particle evaluation system 600 may include remote signal conditioning circuitry such as that which is described in U.S. Pat. No. 4,760,328. In some cases, circuitry may include an impedance matching amplifier. In some cases, a particle evaluation system may include a baseline restorer or additional circuitry. The conduit C can provide a wall of hydrodynamic smoothness, having contiguity at the junction of the first and second peripheral conduit walls (e.g. associated with field amending units 632, 634) with the central conduit wall (e.g. of a central substrate disposed between the field amending units. The conduit C can operate to receive suspended particles therethrough, and can define a central wall region (e.g. provided by substrate 650) disposed between a first peripheral wall region (e.g. provided by field amending unit 632) and a second peripheral wall region (e.g. provided by field amending unit 634). The central wall region typically has an electrical impedance greater than electrical impedances of the first and second peripheral wall regions. In operation, the electrical source provides electrical excitation to the first and second peripheral regions, and the sensing circuit, which is also coupled with the first and second peripheral regions, detects impedance changes within the conduit occasioned by particles passing therethrough.

According to some embodiments, a conductive tube can be connected to a field amending unit of the conduit, which can also serve as a flow restrictor to control flow rate. In some instances, sample volume can be monitored by an insulated electrode or glass capillary fitted with level sensors. For example, an exemplary particle evaluation system may include a 3/16" glass tubing about 6" long. One end of the tubing can be coupled with a two-terminal field-amending/electrode set including a 100-micra Coulter wafer, and an opposing end of the tubing can be coupled with a rubber bulb (e.g. similar to the type used to fill and empty laboratory pipettes). One field-amending element can face outward at the end of the tubing, while the other field amending unit can be sealed inside the tubing, for example where the electrode set is epoxied onto the tubing. The electrode set can be connected with small insulated hook-up wires to electrode leads of a Coulter Counter or similar apparatus. AC signal coupling can be used to separate signals of microvolt level from volt-level excitation voltages across the conduit C. A particle evaluation system may also include a level electrode, which may be provided as a third length of small hook-up wire running down the inside of a stainless steel tubing (e.g. grade or type 316), with the wire from the internal field-amending element serving as a common connection for the outside electrode lead and the level detection wire. Exemplary particle evaluation systems can provide clearly visible pulses (e.g. from a suspension of 10-micra latex particles). It is also observed that pulses may occur as the suspension is expelled from the tube. Further, it is demonstrated that the excitation current is significantly less that with a standard 100-micra Coulter aperture to avoid microbubble generation, requiring higher amplifier gain. What is more, it is shown that fewer "M" pulses and almost no recirculator pulses occurred, this with a smaller coincidence volume. Exemplary particle evaluation systems may also include a mechanism for aspirating analyte, such that operation of the mechanism is matched to flow characteristics of the volumeter conduit.

According to some embodiments, fluid control means 670 may include features of an automatic micropipette, or other devices for performing volume aspiration. In some instances, fluid control means 670 may include features of a hand held micropipette mechanism.

In some instances, the stainless steel 316 tube mentioned above can be acid-passivated to reduce electrochemical interactions with the suspension. According to some embodiments, for example where provided as a disposable part of a hand-held Coulter Counter type device, it is possible to use well-passivated 316 stainless steel tubing for the metal tube and have it coated (for example with glass, or with a polymer cross-linked in situ after application) on the outside to insulate the tube from analyte and then conductively seal such a tube to conductive lead 642 and/or field amending unit 632. In some cases, analogous treatments may be applied to the inside of the stainless steel 316 tube, including a similar seal to conductive lead 644 and/or field amending unit 634, and using a separate (but protected) connection to conductive lead 642 and/or field amending unit 632. For the level detection electrode, it is possible to use another length of smaller tubing, insulated on the outside in the first approach, and inserted to the desired level in the structural tube.

According to some embodiments, particle evaluation systems may operate with reduced noise levels and improved pulse acquisition, despite any higher transimpedance amplification that may be used due to a desire to limit current density between the at-aperture field-amending/electrode elements.

According to some embodiments, a volumeter assembly as disclosed herein can be incorporated into a hand-held instrument containing an integrated or hybrid form of a complete Coulter counter. In some cases, such an instrument may be exclusive of fluidics and glassware. In some cases, such an instrument may include a rubber bulb, a plastic bellows, or some other fluid control means, to draw or express a set volume of sample suspension through the conduit (e.g. conduit C of FIG. 1, 2, 3, 4, or 5). A fluid control means may also be provided in the form of a micropipette mechanism, as discussed elsewhere herein. In some cases, a fluid control means such as a rubber bulb can draw or express a volume of sample suspension through the conduit, for example via a conductive tube-electrode connected to a field-amending element of the conduit. Such a conductive tube-electrode may also serve as a flow restrictor to control flow rate. In some instances, a sample volume can be monitored, for example by an insulated electrode set an appropriate distance up the conductive tube or through use of a glass capillary fitted with level sensors.

In some instances, one or more user-selectable thresholds can be provided, and displayed on a liquid-crystal display. In some cases, a handheld instrument can be dipped into a particle suspension of an appropriate concentration, and such a dipstick Coulter device can be used to accurately count particles in a variety of remote-sampling situations. Although FIG. 6 depicts a conductive tube 620 disposed exterior to an insulative tube 610, as discussed elsewhere herein it is understood that embodiments of the present invention also encompass configurations where the conductive tube is instead disposed interior to the insulative tube. In exemplary embodiments, a combined construct that includes field-amending units, conductive leads or electrodes, and a tube structure (e.g. a sample tube) can be provided as a disposable device.

As mentioned elsewhere herein, where the field amending units are configured to function as aperture excitation electrodes, the allowable aperture excitation current is significantly reduced. Because low aperture excitation currents can be effectively employed, exemplary particle evaluation volumeter assemblies (e.g. two terminal configurations) are well suited for use in producing hand held particle evaluation devices that operate based on the Coulter principle. In many cases, the power requirements involved with effectively exciting such volumeter conduits can be significantly reduced compared with other known aperture based sensing systems. By incorporating the use of lower excitation currents, it is possible to implement particle evaluation systems with more integrated components and smaller hybrid components.

According to certain embodiments, a multi-channel pulse-height analyzer can be provided in an integrated or hybrid form and included in a handheld device. Using a device having tubular ceramic element as discussed with reference to FIG. 6, optionally including a metal tubular sleeve, it is possible to provide a handheld device where the volumeter assembly is present as a two-terminal construct (e.g. FIGS. 1-4), or as a four-terminal construct, such as that which is described in U.S. Pat. No. 6,175,227. In a two-terminal configuration, an excitation current source and sensing circuitry 640 can be operatively connected with the field amending units 632, 634, optionally via respective conductive leads 642, 644 that are coupled with an intermediate substrate 650. In a four-terminal configuration, a pair of excitation electrodes can be positioned remotely from the field amending units and operatively connected with an excitation current source, as described in U.S. Pat. No. 6,175,227. Consequently, a similar device chip may be adapted to a variety of applications. In some forms, it may be desirable to use two-wire methods to couple excitation in to, and pulses out from, the device chip. Such a configuration can permit an operative connection to be made between the respective remote electrodes and the field-amending elements, whereby a functional four-terminal measurement could be made with an apparent two-terminal device.

As discussed elsewhere herein, with the implementation of exemplary two-terminal configurations, the use of hydro-dynamically focused flow into and sweep flow behind the conduit can be minimized or eliminated. Use of the field amending units can also allow elimination of the bulk and expense of associated with other known counters. According to some embodiments, the use of a vacuum source to help pull a sample through a composite volumeter conduit can also allow the conduit to control sample throughflow.

In some instances, a particle evaluation system such as that shown in FIG. 6 can be provided as a minimal AC version and packaged as a remote transducer. Such embodiments can be configured to detect particles in a fluid flow. In some instances, a particle evaluation system such as that shown in FIG. 6 can be provided as a DC version. Exemplary particle evaluation systems can be configured to provide solute-analytic functions, thereby providing a particle detection, sizing, or characterization function as well. In some instances, a small hand-held, battery-powered version (e.g. a dipstick Coulter counter) can be used for marine biology applications. Similarly, exemplary systems can be used in environmental studies at remote sites, and the like. As shown here, such instruments may include a rubber bulb, a plastic bellows, a micropipette assembly, or other fluid control means, to draw or express a set volume of sample suspension through the conduit, for example via a conductive tube-electrode connected to a field amending element of the conduit, which in some instances can also serve as a flow restrictor to control flow rate. Exemplary particle evaluation systems can be configured for sensing and characterizing small particles, and in particular to techniques for detecting and evaluating blood cells or ceramic powders. Often, the particles may be suspended in a liquid medium having an impedance contrast or electrical impedance per unit volume which differs from that of the particles. In many instances, the systems and methods disclosed herein are well suited for use in sensing and characterizing such particles by the Coulter principle.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. In certain cases, method steps or operations may be performed or executed in differing order, or operations may be added, deleted or modified. It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

All patents, patent publications, patent applications, journal articles, books, technical references, and the like discussed in the instant disclosure are incorporated herein by reference in their entirety for all purposes.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

What is claimed is:

1. A system for evaluating particles of a biological sample obtained from an individual, comprising:
    a volumeter assembly having a conduit that receives a fluid suspension containing the particles therethrough, the conduit defining an axial conduit wall length having a central region of electrical resistivity disposed between a first distal region of electrical resistivity lower than the electrical resistivity of the central region and a second distal region of electrical resistivity lower than the electrical resistivity of the central region;

a first chamber in fluid communication with a first orifice of the volumeter assembly conduit, the first chamber containing at least a first portion of the fluid suspension;

a second chamber in fluid communication with a second orifice of the volumeter assembly conduit, the second chamber containing at least a second portion of the fluid suspension; and a current source and sensing circuit module in direct electrical connection with the first and second distal regions of the volumeter assembly, wherein the current source and sensing circuit module provides an electrical excitation current to the first and second distal regions to establish a particle-sensitive zone within the conduit, and wherein the current source and sensing circuit module detects current changes occasioned by particles of the biological sample passing through the particle-sensitive zone.

2. The system according to claim 1, wherein the central region of the conduit wall length is provided by a layer of material having electrical resistivity, and the first and second distal regions of the conduit wall length are provided by a first layer of material having an electrical resistivity lower than that of the layer corresponding to the central region and a second layer of material having an electrical resistivity lower than that of the layer corresponding to the central region, respectively.

3. The system according to claim 1, wherein the conduit wall length is provided by a semiconductor wafer which is doped with an electrically active impurity to provide the central region of higher electrical resistivity disposed between the first distal region of lower electrical resistivity and the second distal region of lower electrical resistivity.

4. The system according to claim 1, wherein the conduit wall length is provided by a unitary assembly having three complementary and contiguous ceramic elements, a center ceramic element of the unitary assembly being substantially pure and two outer ceramic elements of the unitary assembly being either a conductive ceramic or a ceramic infiltrated with a metallic material to enhance the conductivity thereof, and wherein the conduit is formed by through-holes respectively formed in the three ceramic elements.

5. The system according to claim 1, wherein the conduit wall length is provided by a unitary assembly having three complementary and contiguous elements, a center element of the unitary assembly being made of a substantially pure ceramic and two outer elements of the unitary assembly being made of a metallic material, and wherein the conduit is formed by through-holes respectively formed in the three elements.

6. The system according to claim 1, wherein the central region of the axial conduit wall length is provided by a substrate of dielectric material, and the first distal region of electrical resistivity lower than the electrical resistivity of the central region and the second distal region of electrical resistivity lower than the electrical resistivity of the central region are provided by first and second conductive collars, respectively.

7. The system according to claim 1, wherein the volumeter assembly conduit has a circular cross-section.

8. The system according to claim 1, wherein the first and second distal regions of the axial conduit wall length are respectively provided by a material selected from the group consisting of metals of the platinum group, gold, nickel, tungsten, titanium, alloys of the metals, silicon carbide, titanium carbide, and tungsten carbide.

9. The system according to claim 8, wherein the material providing the first distal region differs from the material providing the second distal region.

10. The system according to claim 1, wherein the central region of the axial conduit wall length is provided by a material selected from the group consisting of sapphire, ruby, alumina, quartz, glass, beryllia, silicon carbide, titanium carbide, tungsten carbide, and a lossy dielectric.

11. A method of evaluating particles of a biological sample obtained from an individual, comprising:

transmitting a fluid suspension containing the particles through a volumeter assembly conduit, the conduit defining an axial conduit wall length having a central region of electrical resistivity disposed between a first distal region of electrical resistivity lower than the electrical resistivity of the central region and a second distal region of electrical resistivity lower than the electrical resistivity of the central region;
- providing an electrical excitation current to the first and second distal regions with a current source and sensing circuit module in direct electrical connection with the first and second distal regions, so as to establish a particle-sensitive zone within the conduit, and
- detecting current changes occasioned by the particles of the biological sample passing through the particle-sensitive zone with the current source and sensing circuit module via the first and second distal regions.

12. The method according to claim 11, wherein the central region of the conduit wall length is provided by a layer of material having electrical resistivity, and the first and second distal regions of the conduit wall length are provided by a first layer of material having an electrical resistivity lower than that of the layer corresponding to the central region and a second layer of material having an electrical resistivity lower than that of the layer corresponding to the central region, respectively.

13. The method according to claim 11, wherein the conduit wall length is provided by a semiconductor wafer which is doped with an electrically active impurity to provide the central region of electrical resistivity disposed between the first distal region of electrical resistivity lower than the electrical resistivity of the central region and the second distal region of electrical resistivity lower than the electrical resistivity of the central region.

14. The method according to claim 11, wherein the conduit wall length is provided by a unitary assembly having three complementary and contiguous ceramic elements, a center ceramic element of the unitary assembly being substantially pure and two outer ceramic elements of the unitary assembly being either a conductive ceramic or a ceramic infiltrated with a metallic material to enhance the conductivity thereof, and wherein the conduit is formed by through-holes respectively formed in the three ceramic elements.

15. The method according to claim 11, wherein the conduit wall length is provided by a unitary assembly having three complementary and contiguous elements, a center element of the unitary assembly being made of a substantially pure ceramic and two outer elements of the unitary assembly being made of a metallic material, and wherein the conduit is formed by through-holes respectively formed in the three elements.

16. The method according to claim 11, wherein the central region of the axial conduit wall length is provided by a substrate of dielectric material, and the first distal region of electrical resistivity lower than the electrical resistivity of the central region and the second distal region of electrical resistivity lower than the electrical resistivity of the central region are provided by first and second conductive collars, respectively.

17. The method according to claim 11, wherein the volumeter assembly conduit has a circular cross-section.

18. The method according to claim 11, wherein the first and second distal regions of the axial conduit wall length are respectively provided by a material selected from the group consisting of metals of the platinum group, gold, nickel, tungsten, titanium, alloys of the metals, silicon carbide, titanium carbide, and tungsten carbide.

19. The method according to claim 18, wherein the material providing the first distal region differs from the material providing the second distal region.

20. The method according to claim 11, wherein the central region of the axial conduit wall length is provided by a material selected from the group consisting of sapphire, ruby, alumina, quartz, glass, beryllia, silicon carbide, titanium carbide, tungsten carbide, and a lossy dielectric.

* * * * *